United States Patent
Seaberg et al.

(10) Patent No.: US 9,451,871 B1
(45) Date of Patent: Sep. 27, 2016

(54) DISINFECTING FLOOR MAT

(71) Applicants: Maureen Seaberg, Holbrook, MA (US); Yvonne Makilya, Holbrook, MA (US)

(72) Inventors: Maureen Seaberg, Holbrook, MA (US); Yvonne Makilya, Holbrook, MA (US)

( * ) Notice: Subject to any disclaimer, the term of this patent is extended or adjusted under 35 U.S.C. 154(b) by 0 days.

(21) Appl. No.: 14/798,618

(22) Filed: Jul. 14, 2015

(51) Int. Cl.
*A47L 23/22* (2006.01)
*A47L 23/26* (2006.01)
*A47G 27/02* (2006.01)
*A61L 2/18* (2006.01)

(52) U.S. Cl.
CPC ......... *A47L 23/266* (2013.01); *A47G 27/0206* (2013.01); *A47L 23/22* (2013.01); *A61L 2/18* (2013.01); *B32B 2471/04* (2013.01); *D06N 2209/1671* (2013.01)

(58) Field of Classification Search
CPC ....... A47L 23/00; A47L 23/22; A47L 23/26; A47L 23/266; A47G 27/00; A47G 27/02; A47G 27/0206; A47G 2400/02; A61L 2/00; A61L 2/16; A61L 2/18; A61L 2202/00; A61L 2202/10; A61L 2202/17; B60N 3/04; B60N 3/044; B60N 3/048; D06N 7/0063; D06N 7/00671; D06N 2209/108; D06N 2209/16; D06N 2209/1671; Y10T 428/23993; Y10T 428/23979
USPC ........................ 15/104.92, 104, 93, 215–217; 296/97.23; 422/243, 291, 292; 428/95, 428/96, 101
See application file for complete search history.

(56) References Cited

U.S. PATENT DOCUMENTS

| | | | | |
|---|---|---|---|---|
| 3,300,275 | A * | 1/1967 | Lorman | A47L 23/266 118/264 |
| 5,128,189 | A * | 7/1992 | Bartlett | B32B 1/04 184/106 |
| 5,792,712 | A * | 8/1998 | Hori | A01N 25/34 15/104.93 |
| 6,258,435 | B1 * | 7/2001 | Staal | A01K 1/0157 15/104.93 |
| D478,452 | S | 8/2003 | Kafka | |
| 6,645,597 | B1 | 11/2003 | Swain | |
| 6,886,210 | B2 | 5/2005 | Dean | |
| 7,456,755 | B2 | 11/2008 | Blum | |
| 8,209,811 | B2 | 7/2012 | Jordan | |
| 2002/0031634 | A1 * | 3/2002 | Staal | A01K 1/0157 428/71 |
| 2003/0124935 | A1 * | 7/2003 | Smith | A41D 31/0061 442/239 |
| 2012/0177714 | A1 | 7/2012 | Khoury | |
| 2014/0295537 | A1 | 10/2014 | Omidi | |
| 2016/0015844 | A1 * | 1/2016 | Collins | A61L 2/18 424/411 |

FOREIGN PATENT DOCUMENTS

| | | |
|---|---|---|
| CN | 202413548 | 9/2012 |
| JP | 2012-5589 | * 1/2012 |

* cited by examiner

*Primary Examiner* — Mark Spisich
(74) *Attorney, Agent, or Firm* — Kyle A. Fletcher, Esq.

(57) ABSTRACT

The disinfecting floor mat is a mat that heath care workers and health care visitors step onto when entering or leaving a health care facility. When stepped on the disinfecting floor mat coats the bottom of the footwear of the heath care workers and health care visitors with a disinfecting solution. This disinfecting solution helps to prevent the spread of bacteria within the health care facility. The disinfecting floor mat comprises a top layer, an absorbent layer, a bottom layer, and a disinfecting gel.

12 Claims, 2 Drawing Sheets

US 9,451,871 B1

DISINFECTING FLOOR MAT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of carpet and portable floor mats, more specifically, a floor mat configured for use in disinfecting footwear.

SUMMARY OF INVENTION

The disinfecting floor mat is a mat that heath care workers and health care visitors step onto when entering or leaving a health care facility. When stepped on the disinfecting floor mat coats the bottom of the footwear of the heath care workers and health care visitors with a disinfecting solution. This disinfecting solution helps to prevent the spread of bacteria within the health care facility.

These together with additional objects, features and advantages of the disinfecting floor mat will be readily apparent to those of ordinary skill in the art upon reading the following detailed description of the presently preferred, but nonetheless illustrative, embodiments when taken in conjunction with the accompanying drawings.

In this respect, before explaining the current embodiments of the disinfecting floor mat in detail, it is to be understood that the disinfecting floor mat is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the disinfecting floor mat.

It is therefore important that the claims be regarded as including such equivalent construction insofar as they do not depart from the spirit and scope of the disinfecting floor mat. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
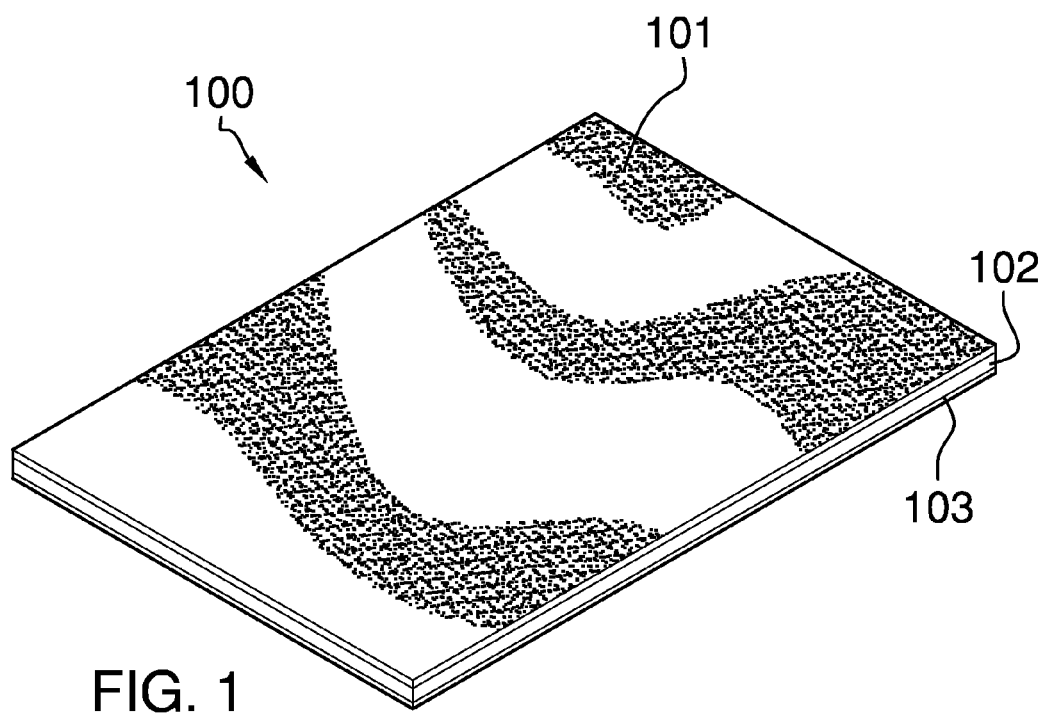
FIG. 1 is a perspective view of an embodiment of the disclosure.
Figure 2:
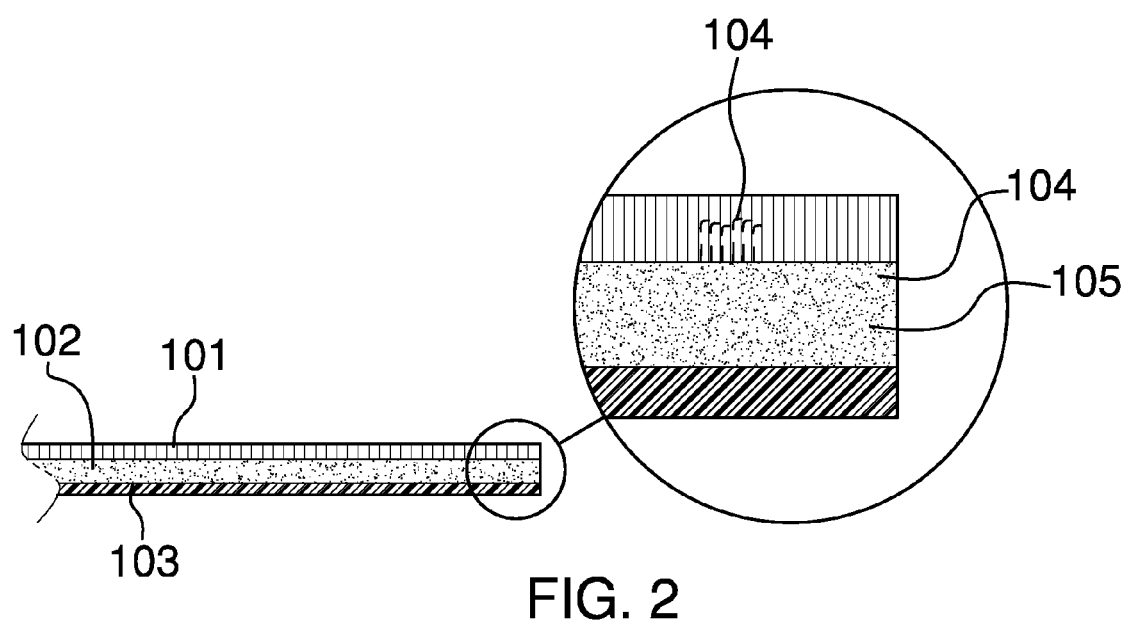
FIG. 2 is a side view of an embodiment of the disclosure.
Figure 3:
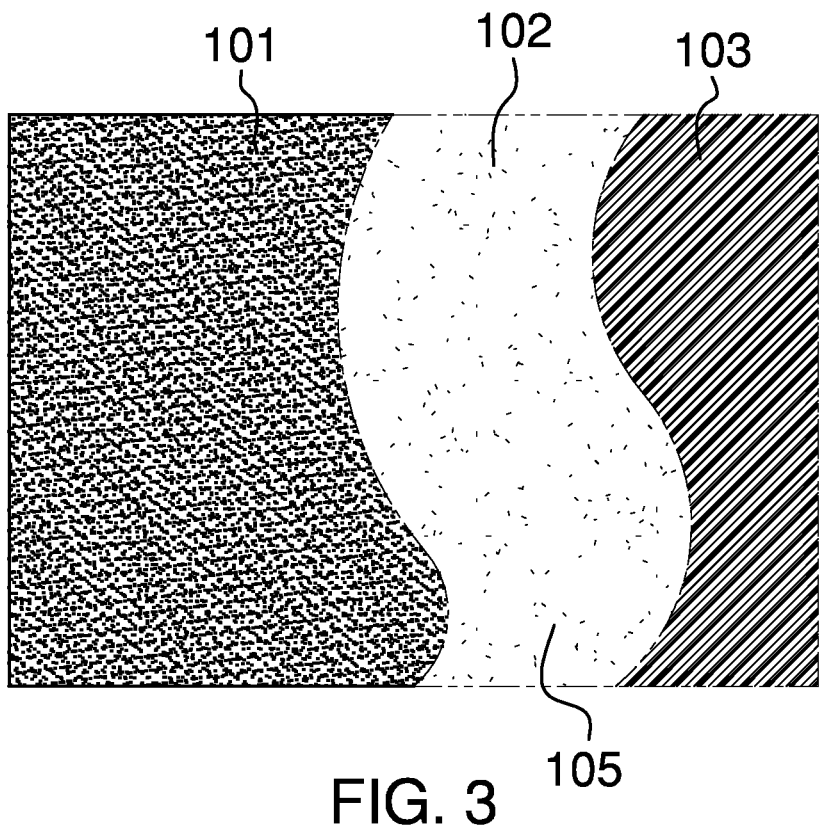
FIG. 3 is a cut-away view of an embodiment of the disclosure.
Figure 4:
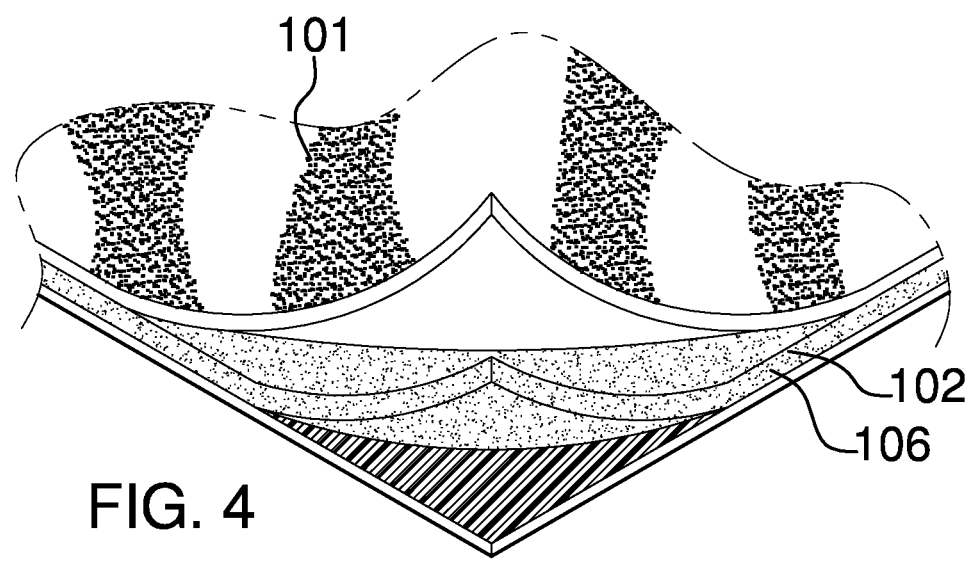
FIG. 4 is an exploded view of an embodiment of the disclosure.

Detailed reference will now be made to potential embodiments of the disclosure, which are illustrated in FIGS. 1 through 4. The disinfecting floor mat 100 (hereinafter invention) is a composite textile device that applies a disinfecting medium 104 to the footwear of a health care visitor that steps upon the invention 100. The invention 100 comprises a top layer 101, an absorbent layer 102, a bottom layer 103, and a disinfecting medium 104.

The top layer 101 is a textile. The top layer 101 is made from a synthetic material that is treated to be stain resistant. The textile pattern used in the top layer 101 is designed to provide a non-slip surface for health care visitors to step on. The top layer 101 is also designed to be permeable to liquids. Suitable fibers to make the top layer 101 include polypropylene, polyester, and polyamide. Polypropylene is preferred for its low cost and wear resistance.

The bottom layer 103 is a sheeting material. The purpose of the bottom layer 103 is to provide a non-skid surface that can rest on the floor of the health care facility. The bottom layer 103 used in the first potential embodiment of the disclosure is a commercially available non-skid rug pad made from felt and rubber.

The absorbent layer 102 is placed between the top layer 101 and the bottom layer 103. The purpose of the absorbent layer 102 is to store the disinfecting medium 104 that will be applied to the footwear of health care visitors. In the first potential embodiment of the disclosure, the disinfecting medium 104 is mixed with one or more viscosity building agents that are used to thicken the disinfectant material into a gel like state. Viscosity building agents may include, but are not limited to, magnesium aluminum silicate or clay like minerals. Clay like minerals include, but are not limited to, kaolinite, halloysites, sodium montmorillonite, calcium montmorillonite, sauconite, vermiculite, nontronite, saponite, hectorite, bentonite, sepiolite, or palygorskite. The disinfecting medium 104 is mixed with the viscosity building agent to form a gel 105. The gel 105 holds the disinfecting medium 104 in suspension and the gel 105 releases the disinfecting medium 104 into the top layer 101 when the pressure of a footstep is placed on the invention 100. In the second potential embodiment of the disclosure, an absorbent material 106, such as an absorbent textile or sponge, is used as the absorbent layer 102. In the second potential embodiment of the disclosure, the absorbent material 106 is soaked in the disinfecting medium 104. The absorbent material 106 is used to soak the disinfecting medium 104 which is released when the pressure of a foot step is placed on the invention 100.

The disinfecting medium 104 is a chemical agent that destroys or inhibits the growth of bacteria or other microorganisms. The disinfecting medium 104 is provisioned in a liquid form so that the disinfecting medium 104 can pass through the top layer 101 to be distributed on the footwear of a health care visitor. Suitable disinfecting mediums 104 include, but are not limited to, peroxygen based disinfectants (such as hydrogen peroxide), aldehyde based disinfectants (such as formaldehyde), quaternary ammonium based compounds (such as ammonia), alcohol based disinfectants (such as ethanol), halogen based disinfectants (such as iodine or hypochlorite), and phenol based disinfectants (such as benzalkonium chloride). The use of hypochlorite is preferred.

To assemble the second potential embodiment of the disclosure, the top layer 101, absorbent layer 102, and bottom layer 103 are cut into a rectangular shape. The top layer 101, absorbent layer 102, and bottom layer 103 are then placed on top of each other so that the edges of the top layer 101, absorbent layer 102, and bottom layer 103 are aligned and the edges of the top layer 101, absorbent layer 102, and bottom layer 103 are sewn together. The disinfectant medium is then poured directly into the absorbent material 106 through the top layer 101.

To assemble the first potential embodiment of the disclosure, a gel 105 is formed from the disinfecting medium 104 and the viscosity building agent. Methods to form gels are well known and documented in the art. Once the gel 105 is formed, it is cut to size. The top layer 101 and the bottom layer 103 are formed so that the shape of the top layer 101 and the bottom layer 103 are slightly larger than the gel 105. The gel 105 is placed between the top layer 101 and the bottom layer 103. The edges of the top layer 101 and the bottom layer 103 are sewn together so as to fully contain the gel 105.

To use the invention 100, the invention 100 is placed in a high traffic area. When health care visitors step on the invention 100 the pressure of the footfall releases the disinfecting medium 104 which is dispensed onto the footwear of the health care visitor.

In the first potential embodiment of the disclosure, when the disinfecting medium 104 is exhausted, the invention 100 is replaced. In the second potential embodiment of the disclosure, when the disinfecting medium 104 is exhausted, the disinfecting medium 104 is replaced by pouring additional quantities of the disinfecting medium 104 through the top layer 101 into the absorbent layer 102.

The following definitions were used in the disclosure:

Composite Textile: As used in this disclosure, a composite textile is a multilayer fabric made of two or more joined layers of textile or sheeting materials.

Elastic: As used in this disclosure, an elastic is an object that deforms when a force is applied to it and that is able to return to its original shape after the force is removed.

Gel: As used in this disclosure a gel refers to a semi-rigid colloidal dispersion of a solid with a liquid or gas.

Microorganism: As used in this disclosure, a microorganism is an organism too small to be viewed by the unaided eye. Microorganisms are usually single celled organisms such as bacteria, viruses, protozoa, fungi and algae.

Sheeting: As used in this disclosure, sheeting is a material, such as cloth or plastic, in the form of a thin flexible layer or layers.

Textile: As used in this disclosure, a textile is a material that is woven, knitted or felted. Synonyms in common usage for this definition of textile include fabric and cloth.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A floor mat comprising:
   a top layer, an absorbent layer, a bottom layer, and a disinfecting medium;
   wherein the top layer, absorbent layer and bottom layer form a composite textile device;
   wherein the floor mat applies the disinfecting medium to the footwear that steps upon the floor mat;
   wherein the top layer is a textile;
   wherein the top layer is designed to be permeable to liquids;
   wherein the textile pattern used in the top layer is designed to provide a non-slip surface for health care visitors to step on;
   wherein the bottom layer is a sheeting material;
   wherein the bottom layer is formed with a non-skid surface;
   wherein the absorbent layer is placed between the top layer and the bottom layer;
   wherein the absorbent layer stores the disinfecting medium;
   wherein the absorbent layer is a gel.

2. The floor mat according to claim 1 wherein the gel is formed as a mixture of the disinfecting medium and one or more viscosity building agents.

3. The floor mat according to claim 2 wherein the viscosity building agent is magnesium aluminum silicate.

4. The floor mat according to claim 2 wherein the viscosity building agent is a combination of one or more compounds selected from a group consisting of kaolinite, halloysites, sodium montmorillonite, calcium montmorillonite, sauconite, vermiculite, nontronite, saponite, hectorite, bentonite, sepiolite, or palygorskite.

5. The floor mat according to claim 2 wherein the disinfecting medium is a chemical agent that destroys or inhibits the growth of microorganisms.

6. The floor mat according to claim 5 wherein the disinfecting medium is a liquid.

7. The floor mat according to claim 6 wherein the disinfecting medium is selected from a group consisting of peroxygen based disinfectants, aldehyde based disinfectants, quaternary ammonium based compounds, alcohol based disinfectants, halogen based disinfectants, or phenol based disinfectants.

8. The floor mat according to claim 5 wherein the disinfecting medium is hypochlorite.

9. The floor mat according to claim 1 wherein the absorbent layer further comprises an absorbent material.

10. The floor mat according to claim 9 wherein the disinfecting medium is a liquid;
   wherein the absorbent layer is soaked in the disinfecting medium.

11. The floor mat according to claim 10 wherein the disinfecting medium is selected from a group consisting of peroxygen based disinfectants, aldehyde based disinfectants, quaternary ammonium based compounds, alcohol based disinfectants, halogen based disinfectants, or phenol based disinfectants.

12. The floor mat according to claim 9 wherein the disinfecting medium is hypochlorite.

* * * * *